United States Patent
Benson et al.

(10) Patent No.: US 8,659,664 B2
(45) Date of Patent: *Feb. 25, 2014

(54) THERMOGRAPHY CAMERA CONFIGURED FOR LEAK DETECTION

(75) Inventors: Robert G. Benson, New Ipswich, NH (US); Thomas J. Scanlon, Hampstead, NH (US); Paul A. Czerepuszko, Hopkinton, MA (US)

(73) Assignee: FLIR Systems, Inc., Wilsonville, OR (US)

( * ) Notice: Subject to any disclaimer, the term of this patent is extended or adjusted under 35 U.S.C. 154(b) by 1238 days.

This patent is subject to a terminal disclaimer.

(21) Appl. No.: 11/726,918

(22) Filed: Mar. 23, 2007

(65) Prior Publication Data

US 2008/0231719 A1    Sep. 25, 2008

(51) Int. Cl.
    *H04N 5/33*     (2006.01)
(52) U.S. Cl.
    USPC ......... 348/164; 348/165; 250/330; 250/338.1
(58) Field of Classification Search
    USPC .......... 348/222.1, 164–166; 250/330, 339.03, 250/338.1, 338.4, 339.01, 332
    See application file for complete search history.

(56) References Cited

U.S. PATENT DOCUMENTS

| | | | |
|---|---|---|---|
| 3,662,171 A | 5/1972 | Brengman et al. | |
| 4,390,785 A | 6/1983 | Faulhaber et al. | |
| 4,496,840 A | 1/1985 | Fabinski et al. | |
| 4,520,265 A | 5/1985 | Griggs et al. | |
| 4,535,639 A | 8/1985 | Bianchini | |
| 4,543,481 A | 9/1985 | Zwick | |
| 4,555,627 A | 11/1985 | McRae, Jr. | |
| 4,745,276 A | 5/1988 | Broicher et al. | |
| 4,772,789 A | 9/1988 | Maram et al. | |
| 4,871,916 A | 10/1989 | Scott | |
| 4,894,526 A | 1/1990 | Bethea et al. | |
| 5,001,346 A | 3/1991 | Barkhoudarian | |

(Continued)

FOREIGN PATENT DOCUMENTS

| | | | |
|---|---|---|---|
| WO | WO 2005/001409 A2 * | 1/2005 | |
| WO | WO 2005/014909 A2 * | 1/2005 | |
| WO | WO 2005001409 A2 * | 1/2005 | |

OTHER PUBLICATIONS

Brochure, Sherlock "Remote gas leak imaging and qualification", published by Gas Imaging Technolgy Buellton CA, USA, no date (www.gitint.com).

(Continued)

*Primary Examiner* — Michael Lee
(74) *Attorney, Agent, or Firm* — Haynes and Boone, LLP

(57) ABSTRACT

A portable camera system (100) includes a lens (104) for forming a focused image of a survey scene (106) onto a focal plane array (108). The focal plane array (108) comprises a cooled two dimensional array of quantum well infrared photo detectors, (QWIP) having a peak spectral responsivity in the wavelength range of 10.4 to 10.8 μm. The camera includes a cooled band pass optical filter (110) having a peak spectral transmittance approximately centered at a wavelength of 10.57 μm and a full width half maximum spectral transmittance bandwidth of approximately 10.3 to 10.7 μm. The camera system (100) is usable to detect an invisible gas plume in a video image of a survey scene if the gas plume contains sulfur hexafluoride ($SF_6$), ammonia, ($NH_3$), Uranyl Fluoride ($U_2O_2F_2$), or any other gas having an absorption band that that at least partially falls within the wavelength band 10.3 to 10.8 μm.

18 Claims, 4 Drawing Sheets

(56) References Cited

U.S. PATENT DOCUMENTS

| | | | |
|---|---|---|---|
| 5,023,685 | A | 6/1991 | Bethea et al. |
| 5,161,408 | A | 11/1992 | McRae et al. |
| 5,225,679 | A | 7/1993 | Clarke et al. |
| 5,255,073 | A | 10/1993 | Wallin et al. |
| 5,264,368 | A | 11/1993 | Clarke et al. |
| 5,317,897 | A | 6/1994 | Jellye et al. |
| 5,386,117 | A | 1/1995 | Piety et al. |
| 5,430,293 | A | 7/1995 | Sato et al. |
| 5,479,258 | A | 12/1995 | Hinnrichs et al. |
| 5,523,569 | A | 6/1996 | Hornfeld et al. |
| 5,637,871 | A | 6/1997 | Piety et al. |
| 5,656,813 | A | 8/1997 | Moore et al. |
| 5,661,590 | A * | 8/1997 | Almogy et al. ............... 359/248 |
| 5,780,724 | A | 7/1998 | Olender et al. |
| 5,824,884 | A | 10/1998 | Olender et al. |
| 5,834,632 | A | 11/1998 | Olender et al. |
| 5,854,422 | A | 12/1998 | McKeon et al. |
| 5,866,073 | A | 2/1999 | Sausa et al. |
| 5,867,264 | A | 2/1999 | Hinnrichs |
| 5,965,899 | A | 10/1999 | Little et al. |
| 6,089,076 | A | 7/2000 | Mueller et al. |
| 6,154,307 | A | 11/2000 | Veronesi et al. |
| 6,157,033 | A | 12/2000 | Chudnovsky |
| 6,327,896 | B1 | 12/2001 | Veronesi et al. |
| 6,355,939 | B1 * | 3/2002 | Dodd ............................. 257/21 |
| 6,642,537 | B1 * | 11/2003 | Gunapala et al. ............... 257/21 |
| 6,657,195 | B1 * | 12/2003 | Martin et al. ............ 250/339.01 |
| 6,680,778 | B2 | 1/2004 | Hinnrichs et al. |
| 6,690,472 | B2 | 2/2004 | Kulp et al. |
| 6,734,452 | B2 | 5/2004 | Gunapala et al. |
| 6,803,577 | B2 | 10/2004 | Edner et al. |
| 6,822,742 | B1 | 11/2004 | Kalayeh et al. |
| 6,866,089 | B2 | 3/2005 | Avila |
| 6,885,965 | B2 | 4/2005 | Butler et al. |
| 6,995,846 | B2 | 2/2006 | Kalayeh et al. |
| 7,022,993 | B1 | 4/2006 | Williams, II et al. |
| 7,030,381 | B2 | 4/2006 | Kilian et al. |
| 7,075,653 | B1 | 7/2006 | Rutherford |
| 7,134,322 | B1 | 11/2006 | Baird |
| 7,151,787 | B2 | 12/2006 | Kulp et al. |
| 7,649,174 | B2 | 1/2010 | Mammen et al. |
| 7,679,046 | B1 | 3/2010 | Benson et al. |
| 2002/0074542 | A1 | 6/2002 | Gunapala et al. |
| 2002/0098592 | A1 | 7/2002 | Neilson et al. |
| 2002/0098593 | A1 | 7/2002 | Nelson et al. |
| 2002/0132360 | A1 | 9/2002 | Neilson et al. |
| 2002/0146836 | A1 | 10/2002 | Neilson et al. |
| 2003/0025081 | A1 | 2/2003 | Edner et al. |
| 2004/0108564 | A1 | 6/2004 | Mitra |
| 2005/0017176 | A1 * | 1/2005 | Koch et al. ................. 250/338.4 |
| 2005/0082520 | A1 * | 4/2005 | Fathimulla et al. ............. 257/14 |
| 2006/0049352 | A1 * | 3/2006 | Irani ........................ 250/339.02 |
| 2006/0091310 | A1 | 5/2006 | Furry |
| 2008/0231719 | A1 | 9/2008 | Benson et al. |
| 2009/0200466 | A1 | 8/2009 | Mammen et al. |
| 2010/0231722 | A1 | 9/2010 | Hill, Jr. et al. |

OTHER PUBLICATIONS

Valenti, Spotting substation gas leaks, Mechanical Engineering, May 2000, pp. 18-22, 29-31. (http://www.memagazine.org/supparch/mepower00/gas/gas.html).

Brochure, Ion Science "SF6 Gascheck P1", published by Ion Science Cambridge UK, no date, (www.ionscience.com).

User Manual (related pages); "ThermaCam GasFind IR" published by FLIR Sytems Inc. North Billerica, MA, USA publication No. 230438-000, Rev B, issue date Jul. 14, 2006.

Wimmers et al. Focal Plane Arrays: Better, Smaller IR Imagers for New Applications, The Photonics Design and Applications Handbook, H-212-217, 1997.

Wimmers et al., "Better, Smaller IR Imagers Lead the Way to New Applications," Photonics Spectra, Dec. 1994, pp. 113-118.

Benson et al., "Thermography Camera Tuned to Detect Absorption of Infrared Radiation in a Selected Spectral Bandwidth", U.S. Appl. No. 12/415,721, filed Mar. 31, 2009, 43 pages.

* cited by examiner

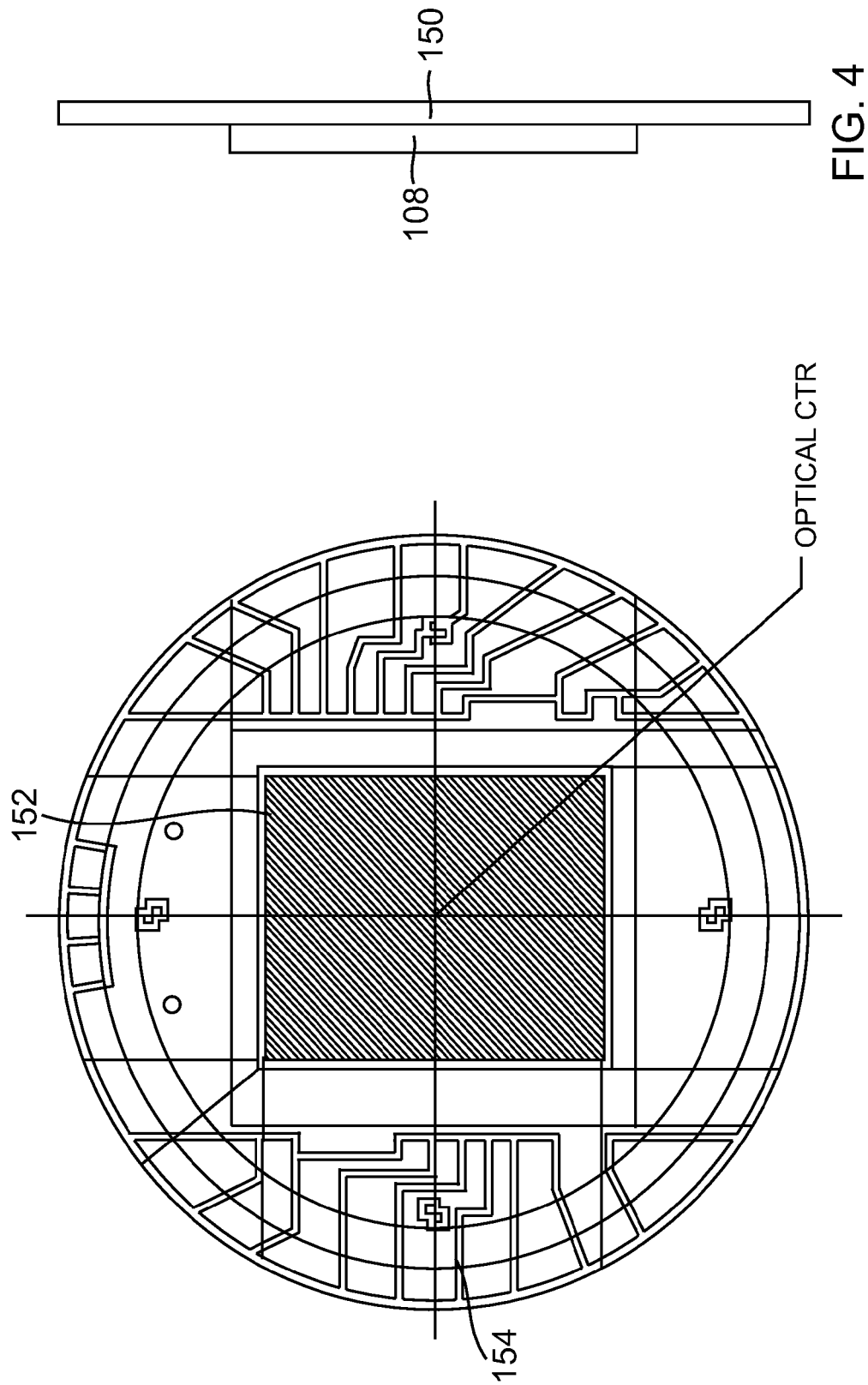

THERMOGRAPHY CAMERA CONFIGURED FOR LEAK DETECTION

BACKGROUND OF THE INVENTION

1. Field of the Invention

The present invention relates to a portable infrared (IR) video camera configured to render and display a video image of an invisible gas plume such as a gas or vapor leaking into the atmosphere from a container or conduit. More specifically the invention is a portable video camera configured to render and display an image of compounds that absorb infrared radiation in the wavelength range of 10.3-10.8 µm.

2. Description of the Related Art

"Leak detection and repair" (LDAR) is a common problem in commercial applications where various substances are processed, stored, distributed, and utilized. In the petrochemical industry, leak detection devices include sniffers, scanners and passive imaging devices configured to identify a petrochemical leak by sensing the absorption of infrared radiation by the leaking compound at one or more predetermined infrared absorption bandwidths. In particular, methane ($CH_4$), has strong infrared absorption bands approximately centered at the non-visible wavelengths 1.33 µm, 1.67 µm, 3.3 µm and 7.6 µm, and it is know to construct leak detecting devices to determine if methane is present in a gas sample by determining if the gas sample absorbs radiation at one or more of the methane absorption wavelengths. Similarly, other compounds can be detected by leak detection devices tuned to determine if other compounds are present in a gas sample by determining if the gas sample absorbs radiation at one or more absorption bands associated with the other compounds.

One example of a sniffer device is disclosed in U.S. Pat. No. 7,022,993 to Williams II et al. The sniffer device draws a gas sample into a chamber through a probe, transmits an infrared radiation beam through the gas sample to a photo detector, and a photo detector response signal is used to determine if the gas sample is absorbing infrared radiation at one or more predetermined absorption bands. One problem with using a sniffer device to detect gas leaks is that the probe must take in a gas sample directly from the leak plume in order to detect the leak. Accordingly, in a large facility or along miles of distribution conduits, leak detection by using a sniffer device is often inefficient and unreliable because leaks can be missed. Moreover, a user must be able to place the probe in the leak plume and this may not always be practical.

One example of a scanner device, called a laser methane detector, is disclosed in U.S. Pat. No. 7,075,653 to Rutherford. The laser methane detector scans a survey area with a tunable IR laser diode emitter and analyzes IR radiation reflected back from the survey area to a photo detector. If the presence of a methane plume is detected in the survey area, the laser methane detector alerts an operator by sounding an audible alarm. The tunable IR laser diode emitter is tuned over a range of wavelengths that includes in-band wavelengths, (approximately 1.67 µm), that are absorbed methane, and out-of-band wavelengths that are not absorbed by methane and to use the photo detector response to determine if methane is present. The laser methane detector provides an advantage over a sniffer because the laser methane detector can detect a methane gas plume from a remote distance. However, one problem with the laser methane detector disclosed by Rutherford is that the tunable IR laser emitter is limited to emitting over a wavelength range of about 1.2-2.5 µm. Accordingly, the laser methane detector is only usable to detect compounds with a strong absorption band within the wavelength range of about 1.2-2.5 µm.

One example of a passive imaging device configured to detect the presence of methane and other hydrocarbon gas plumes is a video thermography camera disclosed in U.S. patent application Ser. No. 11/298,862, by Furry, which was published as US2006/0091310A1 and as WO2005001409. A second example of video thermography camera configured to detect the presence of methane and other hydrocarbon gas plumes is commercially available from FLIR SYSTEM Inc. of Wilsonville, Oreg. and North Billerica, Mass., USA; sold under the trade name ThermaCam® GasFindIR™.

Both example thermography camera examples include a lens positioned to form an image of a survey scene that may contain an infrared absorbing gas plume. The image of the survey scene is focused onto a focal plane array and an optical band pass filter is positioned between the lens the focal plane array to limit the spectral bandwidth of the image of the survey scene to a desired wavelength range. The desired wavelength range corresponds with an absorption band of a compound that it is desired to detect in the image of the survey scene.

The example thermography cameras each include signal processing elements configured to render and display a video image of the limited spectral bandwidth survey scene such that a leak plume that contains a compound having an absorption band corresponding with or at least partially overlapping the limited spectral bandwidth is rendered visible in the displayed video image. A user viewing the displayed video image can then study the leak plume to determine its source or otherwise study its dynamics in real time.

The example thermography cameras each include a cryo-cooler refrigeration device, or container of liquid nitrogen, for cooling the focal plane array and the optical filter, (cold filter), to 77 to 100° K., during operation, in order to reduce thermal energy from radiating from the focal plane array and the optical filter in order to reduce signal noise and increase contract of the leak plume with respect to background elements of the survey scene image.

The example thermography cameras each include a focal plane array that comprises Indium Antimonide, (InSb) IR photo sensor elements. InSb photo sensor elements have a usable responsivity over the approximate spectral range of 1-5.5 µm, but are more practically limited to a usable range of 3.0-5.0 µm. Accordingly, the example thermography cameras are practically limited to detecting leak plume containing compounds that have absorption bands in the spectral range of 3.0-5.0 µm. While that range is suitable for detecting methane and other hydrocarbon compound leaks, there is a need for a thermographic leak detector that operates to detect compounds having absorption bands above 5.0 µm.

Furry suggests using a thermographic camera equipped with an optical filter tuned to wavelengths above 5.5 µm to detect ethylene, (approximately 10.5 µm) propylene, (approximately 10.9 µm), butadiene, (approximately 11.1 µm) and sulfur hexafluoride ($SF_6$), (approximately 10.5 µm), however, Furry is completely silent regarding what focal plane array technology would be suitable for such a thermographic video camera.

Another problem with conventional thermographic leak detection systems is that InSb focal plane arrays have a broad spectral responsivity, e.g. 2 µm, as compared to typical absorption bands, which may have a spectral bandwidth of 0.1-0.3 µm. The problem is that the extra spectral responsivity range of the InSb focal plane arrays contributes dark current signal noise that ultimately reduces the contrast of the leak plume as compared to the background of a video survey image. Accordingly, it is desirable to use a photo sensor that has a spectral responsivity range that is spectrally tuned to the absorption bandwidth of the compound to be imaged in order to increase image contrast.

Additionally, in the other industries, notably electrical power distribution, there is a need for a thermography camera for detecting leaks of the industrial gas sulfur hexafluoride ($SF_6$). $SF_6$ is commonly used as an electrical insulator and has a strong absorption band at approximately 10.57 μm. Conventional thermography cameras do not have a focal plane array capable of forming an image of a survey scene over a wavelength range that includes 10.57 μm.

BRIEF SUMMARY OF THE INVENTION

The present invention overcomes the problems cited in the prior art by providing a portable infrared thermography camera (100) configured to form a video image of a survey scene (106) over a narrow spectral bandwidth of radiation collected from the scene by a camera lens (104). In particular, the camera includes a lens (104) forming an image of the survey scene (106) onto a focal plane array, (FPA), (108). The FPA 108 may comprise a two dimensional array of photo sensor elements configured with sufficient resolution to form a viewable image of the survey scene on a display device, e.g. 320×256 photo sensor elements. The photo sensor elements are configured to provide a spectral responsivity profile having a peak responsivity in the wavelength range 10.4 to 10.8 μm and having a full width half maximum spectral responsivity bandwidth or less than 2.0 μm and preferably less than 0.7 μm. Preferably the FPA (108) comprises quantum well infrared photo sensors (QWIP) tuned to the desired spectral responsivity by constructing quantum well layers alternating with barrier layers having appropriate thickness, spacing, impurity doping and other parameters as may be required. Preferably, the quantum well layers comprise GaAs doped with silicon and the barrier layers comprise AlGaAs but other III-V semiconductor compounds are usable.

The camera (100) includes an optical band pass filter (110) positioned between the lens (104) the FPA (108) for optically filtering radiation collected by the lens to narrow the spectral bandwidth of the focused image formed on the FPA (108). In one example, the optical band pass filter (110) has a peak spectral transmittance in the wavelength range 10.30 μm to 10.70 μm and a less than 0.1% of the peak spectral transmittance outside the wavelength range 10.28 μm to 10.72 μm. In another example, the optical band pass filter (110) has a full width half maximum transmittance bandwidth of 10.40 to 10.80 μm. In addition, the camera (100) includes a refrigeration device configured to cool the FPA (108) and the optical band pass filter (110) to an operating temperature of less than 65° K.

Generally, the camera (100) is used for detecting a gaseous compound in a survey scene when radiation from the scene is by the lens element (104) and passed the optical band pass filter (110) to limit the wavelength range of survey scene energy focused onto the FPA (108) to the wavelength range 10.3 to 10.8 μm. Each sensor element of the FPA 108 generates an analog photo current value according to a photo current responsivity profile and other factors in response to an irradiance generated by the spectrally filtered scene image formed by the lens at the sensor element active surface. The analog photo current values are read out from each photo sensor element and converted to corresponding digital signal values for rendering a video image frame corresponding to the digital signal values.

The video image frames are formatting for display and displayed on a display device (116), e.g. at a standard video rate, for a user to view through an eyepiece (114). Accordingly, a user may point the camera system (100) at a survey scene (106) that may include a gas leak plume comprising compound having an absorption band that at least partially falls within the wavelength band 10.3 to 10.8 μm while observing the display device (116) to determine if there is a gas leak plume visible on the display device.

The camera (100) is usable to detect an invisible gas plume in a video image of a survey scene if the gas plume contains sulfur hexafluoride ($SF_6$), ammonia, ($NH_3$), Uranyl Fluoride ($U_2O_2F_2$), or any other gas having an absorption band that that at least partially falls within the wavelength band 10.3 to 10.8 μm.

BRIEF DESCRIPTION OF THE DRAWINGS

The features of the present invention will best be understood from a detailed description of the invention and a preferred embodiment thereof selected for the purposes of illustration and shown in the accompanying drawing in which:

FIG. 3 illustrates a top view of a focal plane array supported on a support substrate according to the present invention.

FIG. 4 illustrates a side view of a focal plane array supported on a support substrate according to the present invention.

DETAILED DESCRIPTION OF THE INVENTION

Definitions:

The term irradiance as used herein is defined as the total power including all wavelengths of electromagnetic radiation at a surface per unit surface area, and is generally measured in $W/m^2$ or equivalent units.

The term spectral irradiance as used herein is defined as the power per unit area per unit wavelength of electromagnetic radiation at a surface, and is generally measured in $W/m^2/nm$.

The term transmittance as used herein is defined as a ratio expressed as a percentage of radiation intensity transmitted through a medium (I) to radiation intensity incident on the medium ($I_0$), at a specified wavelength. Specifically, an optical band pass filter may have a transmittance of 99.9% at a wavelength of 10 μm and a transmittance of less than 2% at wavelengths less than 9 μm and greater than 11 μm.

The term photo current as used herein is defined as a current generated by a photo sensor in response to irradiance at an active surface of the photo sensor and may be measured in mA.

The term spectral responsivity as used herein is defined as the ratio of photo current generated by a photo sensor per unit irradiance at an active surface of the photo sensor per unit wavelength and may be measured in mA/W/nm or other suitable units.

The term Group III-V semiconductor compounds refers to semiconductor compounds of group III and or group V elements of the periodic table of elements and includes Aluminum phosphide, Aluminum arsenide and Gallium arsenide.

The acronym QWIP as used herein stands for a quantum well infrared photo detector.

Figure 1:
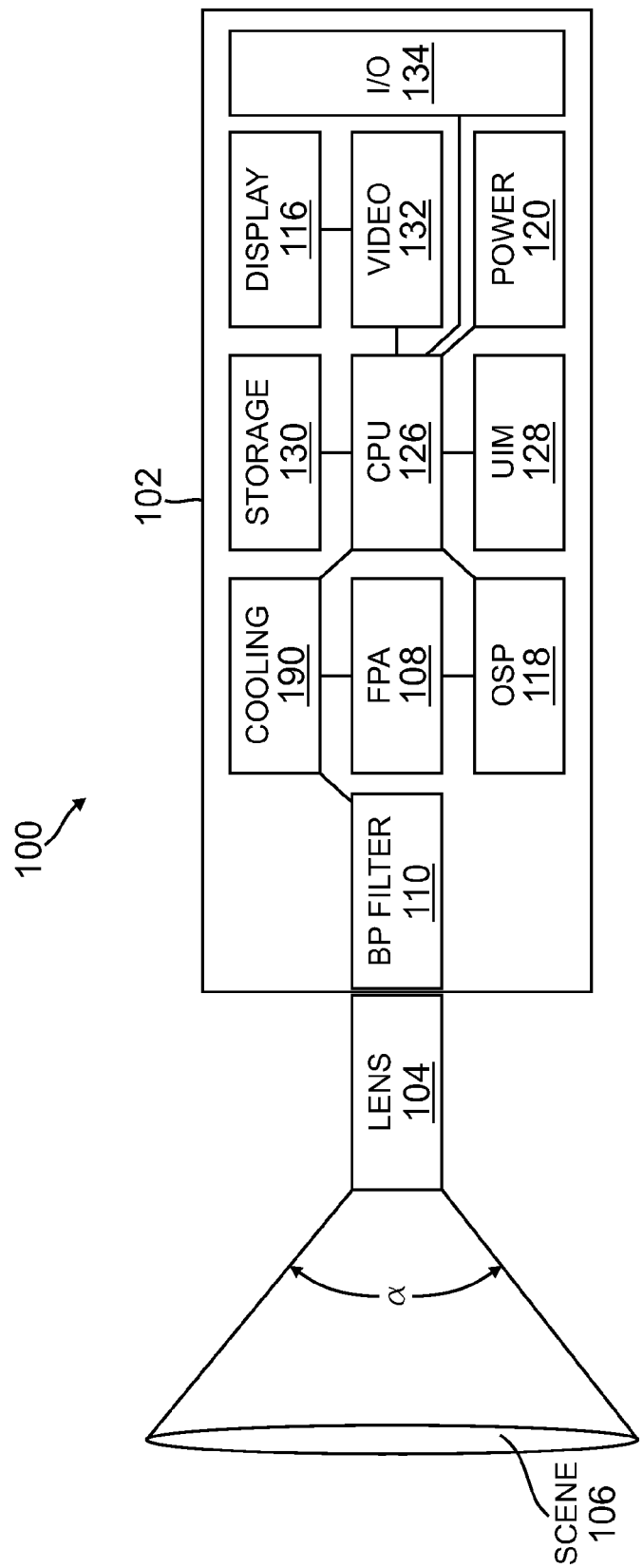
FIG. 1 illustrates a schematic diagram of a camera system according to the present invention.

Referring to FIG. 1 a camera system 100, according to the present invention, comprises a housing 102 and a lens 104 extending out from the housing 102 and the lens and housing are preferably configured with lens mounting hardware configured for removing the lens and attaching other interchangeable lenses as may be required. The lens 104 is configured as in infrared wavelength imaging lens for collecting infrared radiation from a scene 106 over a field of view. The field of view is defined by solid cone angle a, which may be defined by a round aperture inside the lens 104. The lens 104 is configured to form a focused image of the scene 106 onto an active area of a focal plane array (FPA) 108, which is positioned coincident with a focal plane of the lens 104. Preferably the lens 104 and FPA 108 are configured such that the lens 104 forms a focused image of the scene that completely fills the FPA active area.

Generally, the solid cone angle a corresponds with a particular image magnification with larger cone angles corresponding with lower image magnification values than smaller cone angles. The camera system 100 is configured to accept a plurality of interchangeable lenses 104 usable for different situations with each lens being configured to position its focal plane coincident with the active area of the focal plane array 108. The camera 100 may be configured to operate with three different interchangeable lenses 104 with each lens having a different focal length, magnification and corresponding field of view angle a. In one example, a first lens has a focal length of 25 mm and projects a horizontal scene angle α of 22° onto the FPA, a second lens has a focal length of 50 mm and projects a horizontal scene angle a of 11° onto the FPA and a third lens has a focal length of 100 mm and projects a horizontal scene angle a of 5.5° onto the FPA. Preferably each lens 104 is formed from suitable optical materials and aberration corrected over a wavelength range that at least includes 10.4-10.8 μm in order to form a substantially diffraction limited infrared image of the scene 106 onto the FPA active area. Additionally, the lens elements may be coated to reduce reflectivity at a wavelength range that includes 10.4-10.8 μm. Preferably, each lens 104 is constructed with baffles, apertures and the like, and with the optical elements treated with surface coatings in order to prevent stray radiation from reaching the FPA active area. Each lens 104 may also be equipped with an operator adjustable or an automatically adjusted focusing mechanism constructed to adjust the sharpness of the scene image formed on the FPA active area. In addition, the camera system 100 and or lens 104 may include one or more operator adjustable or automatically adjustable mechanical, electrical or electro-optical devices configured to ensure that radiation reaching the FPA 108 is within irradiance limits suitable for rendering an acceptable digital image of the scene. In addition, the camera system 100 may be equipped with a digital zoom system for adjusting image magnification and field of view using digital image zooming techniques.

An optical band pass filter 110 is positioned between the lens 104 and the FPA 108 and functions to limit the spectral band width of radiation reaching the active area of the FPA 108. Specifically, the band pass filter 110 comprises an optical substrate having two opposing and substantially parallel optical surfaces separated by a substrate thickness and formed with a clear aperture usable for spectrally filtering light entering the lens 104 over its widest field of view angle α. The optical filter 110 is positioned with its opposing surfaces oriented substantially parallel to the active area of the FPA 108. Preferably the optical band pass filter substrate comprises optical quality germanium or another suitable substrate with one or both of the opposing surfaces being coated with one or more thin film layers configured to provide a filter spectral transmittance profile that limits the spectral band width of radiation that passes through the band pass filter 110. Alternately, the optical band pass filter 110 may comprise a plurality of optical substrates bonded or otherwise sandwiched together with more than two opposing optical surfaces and more than two surfaces coated with thin film layers.

Typically, the band pass filter 110 has a substantially Gaussian shaped spectral transmittance profile having a peak or near peak transmittance over a first wavelength band, a full width half maximum spectral transmittance separated by a second wavelength range and spectral transmittance profile edges separated by a third wavelength range. In a preferred embodiment, the spectral transmittance profile has a transmittance of less than about 0.1% for wavelengths not included within the third wavelength range defined by the spectral transmittance profile edges.

Preferably, the band pass filter 110 has a spectral transmittance profile that includes a peak or near peak transmittance of 85% substantially at 10.57 μm such that the band pass filter is tuned to an absorption band of the compound $SF_6$. Additionally, in a first embodiment of the band pass filter 110 the spectral transmittance profile has a full width half maximum transmittance bandwidth of approximately 10.4-10.8 μm and spectral transmittance profile edges occurring at 10.38 and 10.82 μm respectively. However a more useful embodiment of the band pass filter spectral transmittance profile is defined in TABLE 1 which is slightly shifted to ensure that the band pass filter includes portions of the absorption band of $SF_6$ approximately centered at 10.57 μm as well as an absorption band of the compound ammonia, ($NH_3$) which has a strong infrared absorption band approximately centered at 10.36 μm. Accordingly, a preferred embodiment of the optical band pass filter 110 has a full width half maximum transmittance bandwidth that overlaps an absorption band of $SF_6$ and $NH_3$.

TABLE 1

| BAND PASS FILTER TRANSMITTANCE | |
|---|---|
| Peak Transmittance (at 10.57 μm) | Greater than or equal to 85% |
| Transmittance at 10.30 um to 10.70 um | 50% of peak transmittance |
| Transmittance from UV–10.28 um | 0.1% |
| Transmittance from 10.72 um–14.0 μm | 0.1% |
| Slope | Less than 2% |

Figure 2:
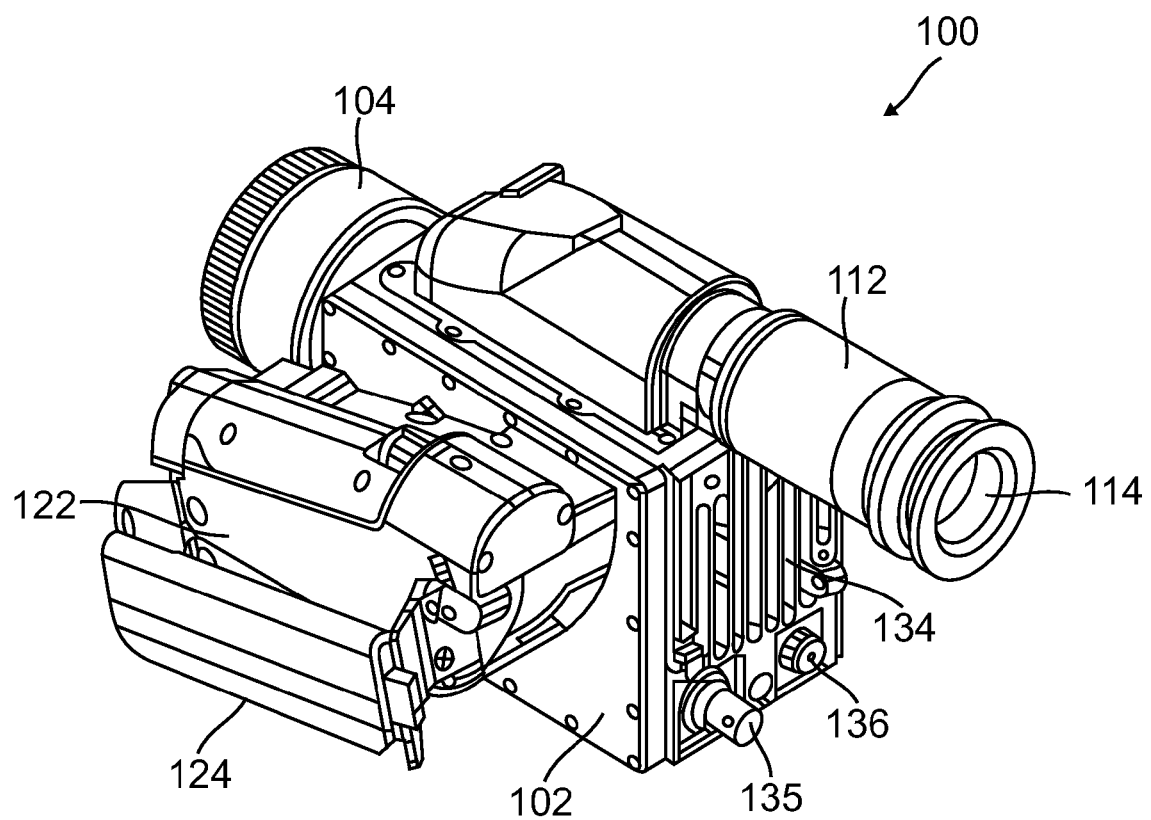
FIG. 2 illustrates an isometric view of a camera system according to the present invention.

Referring now to FIGS. 1 and 2, FIG. 2 depicts an isometric external view of an example embodiment of a camera 100 according to the present invention. The lens 104 is shown extending out from a front end of the camera housing 102 and a view finder assembly 112 extends upward from the housing 102 at a top side thereof The view finder assembly 112 is pivotally supported with respect to the camera housing top side to allow a user to pivot the view finder assembly to a range of viewing positions as may be required. The view finder assembly includes an eye piece opening and eye piece 114 provided to allow a user to view a video display 116, housed inside the camera 100, through the eyepiece. The video display 116 displays a live black and white video image of the scene as formed by the FPA 108 and as processed by an optical signal processor, (OSP) 118. Alternately the video display 116 may display a live color video image of the scene. Accordingly, a user looking into the view finder 112 views the live video image of the scene and adjusts the camera pointing direction, lens focus, digital zoom, and other user controls to view and analyze elements of the scene image as required. Moreover, since the camera system 100 may be used outdoors, the internal display device and eye piece viewing are provided to improve image contrast even in direct sunlight to improve the leak plume detection.

The camera system 100 includes a central processing unit, (CPU) 126 interconnected with a digital data storage module 130, a user interface module (UIM) 128, a power module 120, a cooling or refrigeration module 190 an optical signal processing module (OSP) 118, a video driver module 132, and an associated video display device 116. The CPU 126 interfaces with the digital data storage module 130 to exchange digital data therewith for receiving operating program steps stored in the storage module 130 and executing the operating programs steps in accordance with preset operating modes and conditions and further in accordance with user input commands received from a user through the UIM 128.

Generally, the camera system 100 operates to form an image of a survey scene onto the FPA 108, render a digital image of the survey scene in a video image frame format, display the video image frame on the display device 116 or deliver the video image frame out of the camera system 100. Alternately, video image frames can be stored on the digital data storage device 130. In addition, the camera system 100 is configured to update video image frames at one or more video frames rates ranging from 15-100 cycles per second.

The CPU 126 may comprise a commercially available integrated circuit microprocessor chip and the microprocessor chip may include digital data processing hardware, memory registers and cache memory for temporary data storage.

The digital data storage module 130 may comprise one or more permanently installed or removable memory devices using solid state, optical or magnetic memory storage devices including solid state random or dynamic access memory (RAM, DRAM), non-volatile FLASH memory, optical compact disk memory, (CD) digital video disk memory (DVD), magnetic hard or soft disk memory and the like.

The UIM 128 comprises a plurality of user interface control elements such as one or more toggle switches, variable position dials, knobs, key pads, or the like, positioned on external surfaces of the housing 102 and ideally positioned for ergonomic operation of the camera system 100 while looking through the eyepiece 114. The user interface control elements allow a user to select various camera operating modes, power modes, lens modes, video display modes, and the like, as may be required. Each user selection includes the actuation of a user input device and a signal generated by the actuation and communicated to the CPU 126 to reconfigure camera operation according to user input commands. In addition, the UIM 128 may interface with a video driver 132 to display text and graphics on the video display device 116 such as for displaying menus, status indicators, warnings, or the like in a text and graphic form that is easily interpreted by a user viewing the display device 116 through the eyepiece 114. The text and graphics may be displayed on the video display device 116 simultaneously with a live or still video image of the survey scene received from an optical signal processor 118 such that camera operating conditions and the like can be displayed at edges of the display screen during live imaging by the camera system 100. Alternately, the entire display device 116 may be filled with a menu, or the like, to allow the user to set or review various camera parameters, conditions, or settings. Accordingly, a user may operate the camera 100 to view a live scene image while simultaneously viewing camera status and mode conditions through the eyepiece 114 and the user may use fingers and thumbs to actuate switches/actuators/keypads and the like disposed on outside surfaces of the camera housing 102 to adjust or reset camera operating conditions while viewing a live image.

The camera system 100 includes power module 120 and an input output (I/O) module 134. The power module 120 comprises a battery and other power distributing and conditioning elements. The battery is housed in a battery compartment generally indicated by reference numeral 122. The battery compartment 122 also serves as a user handle and includes a flexible strap 124 attached thereto to provide improved user gripping. The front side of the battery compartment includes a hinged door, not shown, through which the rechargeable battery can be installed and removed. The battery may comprise a commercially available high capacity rechargeable Nickel Metal Hydride (NiMH), Nickel Cadmium (NiCd), or Lithium Ion (LiION), battery and the camera system 100 may be sold with a separate battery charger. Alternately, any other self contained power source may be used to provide a source of power to the camera system 100. Additionally, the power module includes one or more input terminals, associated with an I/O module 134, for receiving power inputs from a DC power source, such as a vehicle power system, or from an AC power source such as a conventional building power system. The power inputs may be used to operate the camera directly, to recharge a battery installed in the battery compartment 122, or both. The power module 120 may also include control systems such as sensors, switches, power conditioning elements, and the like, all interfacing with the CPU 126 and operable according to power module program operating steps stored in the digital data storage module 130. Generally, the power module 120 interfaces with and distributes power to camera systems that require power and may shut off automatically or reduce power consumption when appropriate.

The I/O module 134 includes various wire connecting ports extending through the camera housing 102 and interfacing with internal systems and may include a wireless transceiver for communicating with external devices over radio or microwave frequencies. In particular, the I/O module 134 includes power input ports, a digital video output port 135 for interfacing with an external video display device and an analog video output port 136 for interfacing with a video storage and or display device configured to receive separate video, (S-video). In particular, the camera system 100 may be sold with a separate video recording device usable to store and display video images for remote viewing.

Referring to FIGS. 3 and 4, the FPA 108 is shown mounted on a support substrate 150. The FPA 108 includes an active area 152 comprising a two dimensional array of photo sensor elements. The active area is positioned in a focal plane of the lens 104 and receives radiation from the scene 106 through the lens 104 and optical band pass filter 110.

Each photo sensor is constructed to generate a photo current or other electrical photo signal in response to radiation falling thereon. The amplitude of the photo current is proportional to the irradiance and wavelength of radiation incident on the sensor surface. Ideally, each sensor in the array has a substantially uniform responsivity profile, e.g. photo current amplitude, generated in response to a given irradiance at a given wavelength. However in practice, the responsivity profile of individual sensor elements varies from element to element and must be corrected using a calibration function. Each photo sensor may generate a substantially linear photo current output over a limited range of input irradiance and a non-linear photo current output outside the linear range. Accordingly, the camera system 100 may include devices constructed to maintain sensor irradiance within the range that produces a linear photo current output, and or the camera system 100 may include electronic or digital systems configured to render a corrected image when irradiance levels at the sensor surfaces are outside the desired operating range.

Sensor elements of the active area 152 are arranged in a two dimensional array of rows and columns. In one example, the active area 152 comprises and array of 320×256 sensing elements with approximate array dimensions 9.6×7.7 mm and with each sensor element centered within a unit cell having approximate dimensions of 30 μm×30 μm. The FPA 108 further includes a conventional silicon complementary metal-oxide-semiconductor (CMOS) readout integrated circuit 154 positioned between the active area 152 and support substrate 150 and interconnected to each individual sensor element through an indium bump, or other suitable connector, extending between each sensor element and the readout circuit 154.

The FPA 108 and CMOS readout integrated circuit 154 are bonded or otherwise attached to the support substrate 150. The support substrate 150 comprises an electrically insulating material such as a sapphire or alumina substrate. In one example, the support substrate 150 is circular having an outside diameter of approximately 21.1 mm, (0.83 inches) and a thickness of approximately 0.5 mm, (0.197 inches) and supports the active area 152 substantially centered on the support substrate 150. The CMOS readout integrated circuit 154 is configured to integrate individual sensor photo current responses over time and to periodically deliver an integrated signal value out from the circuit 154 to the optical signal processor (OSP) 118. The read out circuit 154 also applies a bias voltage to sensor elements and may include an electrical gain circuit and other circuit elements for amplifying and otherwise modifying sensor photo response signals as may be required. In addition, parameters of the integrated circuit 154, particularly integration time, may be controlled by the CPU 126 and modified according to image conditions, user input commands, or both.

The signals are delivered out from the readout integrated circuit 154 over wire bonded connections extending between terminal points on the circuit 154 and electrical output terminals 156. Each output terminal 156 may be associated with a plurality of individual photo sensor elements, e.g. an entire row or column of sensor elements. The electrical terminals 156 extend from inside a dewer assembly, shown in FIG. 5 and described below, to a connector interface suitable for connection with the OSP 118.

The OSP 118 includes circuits configured to digitize individual sensor element photo signals by converting each an analog signal received from each photo sensor to a digital equivalent black and white grey scale gradation value, or the like. Each gradation value is a whole number ranging from a minimum value for white corresponding with a selected minimum photo sensor response signal and a maximum value for black corresponding with a selected maximum photo sensor response signal and with intermediate values corresponding with intermediate grey scale levels according to a substantially linear scale. Typical digital grey scale values range from 1 to 256 or 1 to 64K, however other ranges are usable. For each video frame, the OPS 118 assigns each sensor element with a grey scale pixel value corresponding with the irradiance generated by the survey scene at the sensor element and assembles the video frame for storage in a frame buffer or delivery out from the OSP. The video image may be rendered with one pixel corresponding to each sensor element or with more than one sensor element being associated with each pixel.

The OPS 118 is configured to apply biases and or corrections to individual pixel values in order correct for differences in sensor element to sensor element responsivity profiles, to adjust the dynamic range of the image, to account for non-scene noise generated by a bias voltage applied to the sensor elements, to change the video frame rate, to filter out noise or static non-scene image artifacts, and to make other adjustments as may be required in order to enhance the video image and to extract as much scene information from the image as can be used. Additionally, the OSP 118 is configured to contour the video image by rendering a video image with a compressed grey scale range for displaying scene energy contours. Alternately, the OPS 118 is configured to assign colors to grey scale gradation values or groups of grey scale values to render a color image of the scene with different colors corresponding to different senor irradiance values. Moreover, the OPS 118 is configured to reverse gray scale values for generating reverse images and may apply other adjustments to the linearity of gray scale value assignment in order to extract as much scene information from the image as can be used.

Once each scene video image is assembled and corrected by the OSP 118, the scene video image is delivered to the video driver 132 or may be delivered out from the camera system 100 through the I/O module 134. The video driver 132 formats the scene video image for display on the camera internal display device 116 or for display on an external display device connected to the I/O module connector 135. The video driver 132 is configured to add text and graphics to each video image in order to display information on the display device 116 simultaneously with the display of a video image of the scene 106. The displayed information may comprise a camera operating mode, high or low irradiance warnings, focus conditions, lens type, imaging mode parameters and other conditions as may be useful. Additionally the video driver 132 may be configured to display a cursor or other movable display element over the video image being displayed. In one example, a cursor may be locked to an image feature, e.g. the brightest pixel in the image, and the cursor may follow the position of the brightest pixel in the image as each video frame is updated. Additionally, the video driver 132 may be configured to display a menu on the display device 116 and to receive commands from a user interface keypad, or the like, for displaying user entries or for moving a cursor over the displayed menu in response to a user's commands. Additionally the video driver 132 may be configured to display individual video image frames, to display a plurality of video image frames in a thumb nail display mode, and or to display a still or video images in other modes as may be required. Additionally, the video driver 132 may be configured to display date, time, camera global position coordinates, scene names and or any other information that may be useful. Additionally, the camera 100 may be configured to store one or more video image frames, including any text or graphic information displayed simultaneously with the video image on the camera storage module 130, or to deliver video image frames out of the camera through the I/O module 134.

Figure 5:
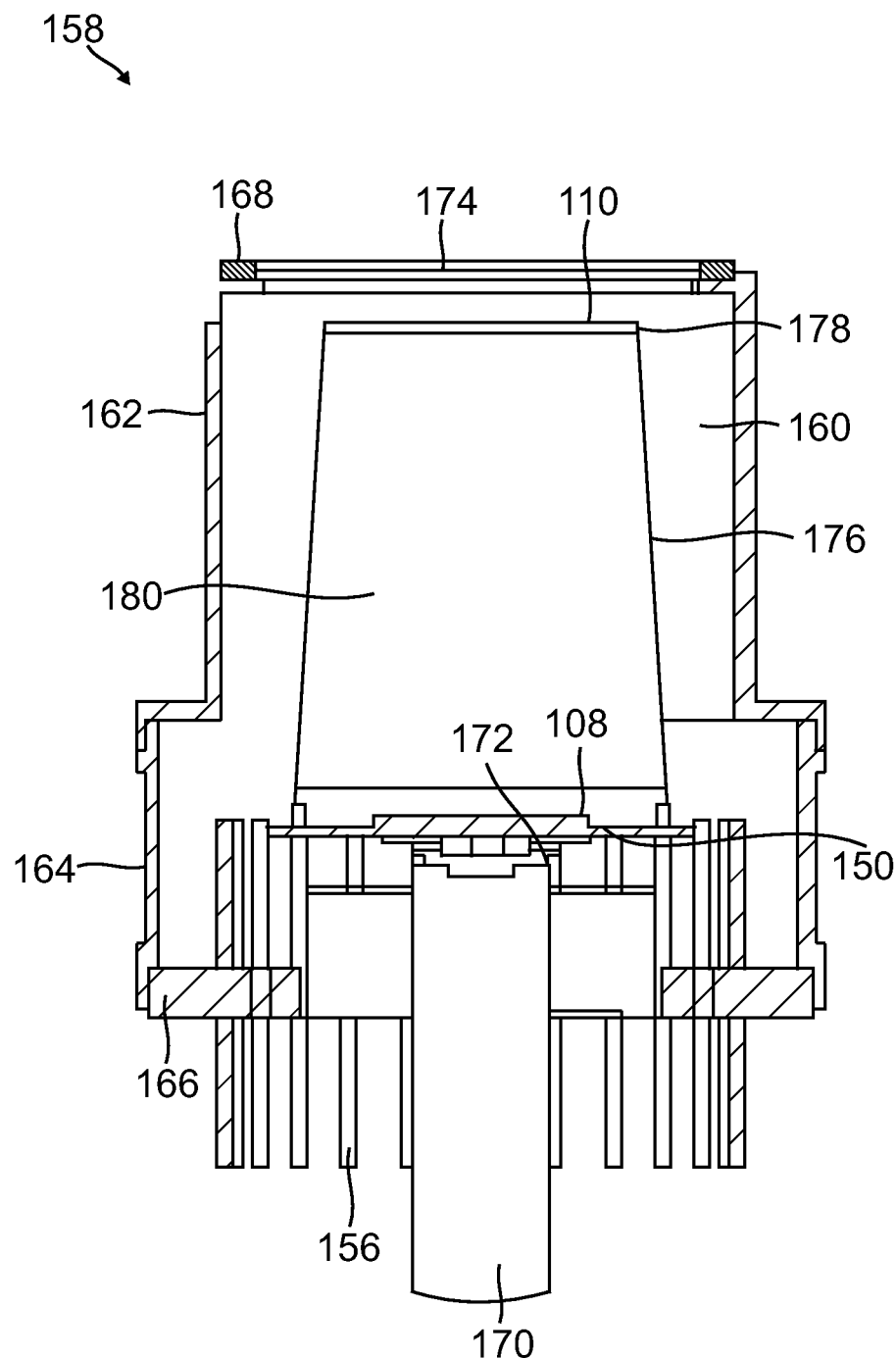
FIG. 5 illustrates a section view taken through a dewar assembly according to the present invention.

Referring now to FIG. 5, a section view shows the support substrate 150 and FPA 108 supported inside a dewar assembly, generally indicated by reference numeral 158. The dewar assembly 158 generally encloses a substantially cylindrical hollow vacuum cavity 160 formed by annular sidewalls 162 and 164, a base wall 166 and a top wall 168, all laser welded or otherwise suitably joined together to provided the vacuum tight enclosure 160 which is drawn to a low vacuum pressure e.g. $10^{-8}$-$10^{-10}$ Torr. The base wall 166 includes a sealed aperture passing there through for receiving a cold finger 170 into the vacuum cavity 160 and the cold finger is formed with a thermally conductive end cap 172 configured to attach to and support the support substrate 150. The dewar assembly top wall 168 includes an aperture passing there through for receiving an IR transparent window 174 therein and supported by the top wall 168. The transparent window 174 admits IR radiation received from the lens 104 into the hollow vacuum cavity 160.

A stray light baffle 180 comprises an annular sidewall 176 extending between the support substrate 150 and a light baffle top wall 178. The light baffle top wall 178 includes an aperture passing there through and the optical band pass filter 110 is supported within the aperture by the light baffle top wall 178. The stray light baffle 180 is formed from a thermally conductive material with the annular side wall 176 formed cone-shaped such that the annular side wall 176 and a clear aperture of the band pass filter 110 work together to limit radiation falling onto the FPA active area 152 to only radiation received from the field of view of the lens 104. Additionally surfaces of the light baffle 180 are shaped and treated to absorb or otherwise prevent stray radiation, e.g. reflected or emitted from other local surfaces from reaching the active area 152.

The cold finger 170 extends from a high performance Sterling cycle refrigeration device housed within the camera system housing 102. The refrigeration device operates to cool the end cap 172 to a temperature of approximately 65K or less and preferably 55° K. The end cap 172 is positioned in contact with the support substrate 150, which provides an efficient thermally conductive pathway extending from the end cap 172 to the FPA 108 and to the light baffle annular wall 176. Additionally, the light baffle annular wall 176 provides an efficient thermally conductive pathway to the band pass optical filter 110. After an initial cool down period, e.g. 1-10 minutes depending upon the thermal load, the refrigeration device draws enough thermal energy away from the FPA 108, stray light baffle and optical band pass filter 110 to substantially cool each element to an operating temperature of approximately 55° K. This prevents the cooled element from emitting a radiation signal that may be detectable by the active area 152, and in the case of the FPA 108 from generating a thermally induced electrical signal (dark current) that may contribute unwanted electrical noise to the scene image. Thus according to one aspect of the present invention, the FPA 108, light baffle 180, and optical band pass filter 110 are cooled to an operating temperature of approximately 55° K. Moreover, the evacuated vacuum cavity 160 acts as a thermal insulator to thermally isolate the cooled elements from the ambient surroundings.

In a further aspect according to the present invention, each individual sensor of the FPA 108 comprises a quantum well infrared photo detector, (QWIP) having a peak spectral responsivity approximately in the range of 10.4-10.8 µm and having a full width half maximum spectral bandwidth of less than 1.0 µm and preferably less than about 0.7 µm. More specifically, each QWIP photo sensor is constructed with a spectral responsivity at 10.6 µm that is at least 80% of the peak spectral responsivity. Generally the QWIP is constructed from III-V compound semiconductors such as gallium arsenide, (GaAs), and aluminum gallium arsenide (AlGaAs) formed in thin alternating layers of GaAs quantum wells, and AlGaAs barriers. The well layers are doped with electron donor impurities, e.g. silicon, or other suitable doping materials, to generate a desired flow of free electrons in the well layers. Generally the peak response wavelength and the spectral band width of the photo response of a QWIP detector is determined by the thicknesses and compositions of the well and barrier layers. Accordingly, the thickness and composition of the QWIP layers of the present invention are selected to absorb photons with wavelengths in the range of 10.4 to 10.8 µm to generate a peak photo current in response to absorbing such photons. However, with responsivity tuned to the wavelength range of 10.4 to 10.8 µm the susceptibility of the QWIP detector to generate an undesirable dark current is increased as compared to detectors having responsivity at smaller wavelengths such as the 3.0-5.0 µm range used for methane imaging.

Generally dark current is the current generated by a photo sensor in response to a substantially negligible irradiance received from a survey scene, (e.g. with the lens cap blocking the camera lens), such that dark current is signal noise. Dark current is generated in response to IR radiation that is emitted by the FPA 108, the support substrate 150, the light baffle 180 and the optical filter 110. The spectral bandwidth of the IR radiation emitted by local elements depends on the absolute temperature of the local elements and according to the present invention, the local elements are maintained at an absolute temperature of less than 65° K. in order to reduce the amount of IR radiation that the local elements emit in the wavelength range of 10.4 to 10.8 µm. Ideally the local elements are maintained at an absolute temperature of less than 55° K.

Generally the camera system 100 operates to render a video image of a scene. While radiation energy received from the scene may have a wide spectral bandwidth, the FPA 108 is constructed with QWIP photo sensors that generate a peak photo current response in the wavelength range of 10.4 to 10.8 µm and to have a full width half maximum spectral bandwidth of less than 2.0 µm and preferably with a spectral bandwidth of 0.7-1.0 µm. This reduces signal noise generated by the background of the scene and by elements of the camera itself to increase contrast between a leak plume and the scene background. The camera 100 preferably includes narrow band pass optical filter 110 having a peak transmittance within the wavelength range of 10.30 to 10.70 µm and having considerably less transmittance, e.g. 0.1 % of the peak transmittance outside the wavelength range of 10.28 µm to 10.72 µm. Other optical filter spectral transmittance profiles that include the spectral range 10.4-10.8 µm are also usable. The focal plane array 108, band pass filter 110 and other local support elements are enclosed in a vacuum cavity to thermally isolate them from the camera body and surrounding air and cooled to 65° K. or less by a refrigeration device housed with the camera system to further reduce dark current in the FPA 108 and to reduce thermal radiation from elements surrounding the FPA 108.

Generally all areas of a scene include some level of radiation in the spectral bandwidth 10.3-10.8 µm, except that areas of the scene that are absorbing radiation in the spectral bandwidth 10.3-10.8 µm will have less radiation in that spectral bandwidth range than other areas of the scene. Accordingly when the scene is imaged onto the FPA 108 and filtered by the band pass filter 110, areas of the scene having low radiation levels will generate the low irradiance levels at corresponding sensor surfaces and will generate low photo currents in the FPA 108. Accordingly area of the scene that are absorbing radiation that falls within the narrow bandwidth of the scene image (10.3-10.7 µm or 10.4-10.8 µm depending on the optical filter used) will be readily distinguishable from other areas of the scene when the scene image is render as a video image and viewed by a user. Accordingly, compounds, (gasses, liquids or solids) having an infrared absorption band that at least partially overlaps the spectral band 10.3 to 10.7 µm, (or 10.4 to 10.8 depending on the filter used) can be viewed in the scene image.

One example compound that can be imaged using the thermography camera system 100 of the present invention is sulfur hexafluoride ($SF_6$) which has a strong infrared absorption band that extends from about 10.51-10.65 µm with a peak absorption approximately centered at 10.57 µm. $SF_6$ is a gas used as an electrical insulator in power distribution equipment and the like, as a cover gas over molten magnesium to minimize oxidation, and as an agent for improving process performance in semiconductor manufacture. Additionally $SF_6$ is a potent greenhouse gas that may contribute to environmental damage when it is released e.g. by leaks.

Another example compound that can be imaged using the thermography camera system 100 of the present invention is ammonia, ($NH_3$) which has a strong infrared absorption band approximately centered at 10.36 μm. $NH_3$ is used as a reagent to produce nitric acid, as a fertilizer, as a refrigerant, as a disinfectant, a solvent, and has many other uses. However ammonia is toxic to mammals and may be harmful when released e.g. by leaks.

Another example compound that can be imaged using the thermography camera system 100 of the present invention is uranyl fluoride ($UO_2F_2$). $UO_2F_2$ is created when uranium hexafluoride ($UF_6$) leaks into the atmosphere. $UF_6$ is a gaseous compound used in uranium enrichment and is the compound that most depleted (waste) uranium is converted to for long term storage in gas cylinders. It is desirable to detect and repair leaks in $UF_6$ containers and to look for $UF_6$ to detect uranium enrichment activity by detecting the local presence of uranyl fluoride ($UO_2F_2$).

According to one aspect of the present invention, an image of a scene 106 is collected by the lens 104, spectrally band pass filtered by the optical filter 110, focused onto the FPA 108 by the lens 104, rendered as a video image by the OSP 110, configured for display by the video processor 132 and displayed by the video display device 116. More specifically, the image focused onto the FPA has a spectral bandwidth in the range of 10.3-10.7 or 10.4-10.8 μm depending on the spectral transmittance of the optical filter 110. The video image is rendered by assigning the lowest levels of photo current generated by the FPA in response to the image focused onto the FPA the lowest grey scale values, by assigning the highest levels of photo current generated by the FPA in response to the image focused onto the FPA the highest grey scale values and by assigning intermediate levels of photo current generated by the FPA in response to the image focused onto the FPA intermediate grey scale values in a substantially linear distribution of grey scale values.

According to another aspect of the present invention, the camera system 100 may be operated to reverse the grey scale polarity of video images of the scene by assigning the highest grey scale values to the lowest levels of photocurrent.

According to another aspect of the present invention, the camera system 100 may be operated to render color video images of the scene by assigning a different color to different levels of photocurrent.

It will also be recognized by those skilled in the art that, while the invention has been described above in terms of preferred embodiments, it is not limited thereto. Various features and aspects of the above described invention may be used individually or jointly. Further, although the invention has been described in the context of its implementation in a particular environment, and for particular applications, e.g. imaging gas leak plumes for compounds having absorption bands approximately in the spectral bandwidth of 10.3-10.8 μm, those skilled in the art will recognize that its usefulness is not limited thereto and that the present invention can be beneficially utilized in any number of environments and implementations including but not limited to any other application wherein it would be useful to generate a video image of a compound having an absorption band that can be detected by a QWIP or other narrow spectral bandwidth detector tuned to the absorption band of the compound. Accordingly, the claims set forth below should be construed in view of the full breadth and spirit of the invention as disclosed herein.

The invention claimed is:

1. A camera system configured to render a video image of a scene, the camera system comprising:
   a lens element having a field of view for collecting radiation from the scene and forming a focused image of the scene at a focal plane;
   a focal plane array, disposed substantially coincident with the focal plane, comprising an active area formed by a two dimensional array of quantum well infrared photo detectors (QWIPs) each having an active surface and each generating a photo current responsivity profile in response to an irradiance at the active surface, wherein the QWIPs are tuned using alternating layers of quantum wells and barriers to have a photo current responsivity profile having a peak response within a wavelength range of 10.4 μm to 10.8 μm and a full width half maximum spectral bandwidth of less than 0.7 μm;
   a narrowband optical filter positioned between the focal plane array and the lens element and having a peak transmittance within the wavelength range of 10.4 μm to 10.8 μm;
   a housing for enclosing the focal plane array therein and for supporting the lens element attached to a surface thereof;
   a readout, contained within the housing and associated with the focal plane array, for reading a photo current output from each QWIP; and
   a signal processor, contained within the housing, for receiving the photo current output from each QWIP from the readout, for converting the photo current output from each QWIP to a digital signal value, and for rendering a video image of the scene in accordance with the digital signal values, wherein the less than 0.7 μm spectral bandwidth of the focal plane array is selected to reduce signal noise substantially outside the wavelength range of 10.4 μm to 10.8 μm associated with the optical band pass filter and/or the focal plane array.

2. The camera system of claim 1, wherein:
   the narrowband optical band pass filter has a transmittance of 0.1% or less of the peak transmittance outside the wavelength range of 10.4 μm to 10.8 μm; and
   the less than 0.7 μm spectral bandwidth of the focal plane array is selected to reduce dark current associated with the optical band pass filter and/or the focal plane array.

3. The camera system of claim 2 further comprising a refrigeration device contained within the housing and configured to cool the focal plane array and the optical band pass filter to an operating temperature of less than 65° K.

4. The camera system of claim 1 wherein
   the quantum well layers comprise GaAs doped with silicon to generate a desired flow of free electrons in response to the radiation and wherein
   the barrier layers AlGaAs.

5. The camera system of claim 2 further comprising a vacuum tight enclosure formed to enclose the focal plane array and the optical band pass filter in a vacuum cavity drawn down to a vacuum pressure to thermally insulate elements contained with the vacuum cavity.

6. The camera system of claim 5 further comprising a video driver and a video display device, each contained within the housing, and wherein the video driver receives the video image from the signal processor and formats the video image for display on the display device.

7. The camera system of claim 6 further comprising a user interface module comprising actuator elements disposed on external surfaces of the housing for converting user actions into input commands suitable for operating the camera system in one or more operating modes.

8. The camera system of claim 7 further comprising a power module that includes a rechargeable battery attached to the housing for operating the camera system as a portable device.

9. A method for detecting a gaseous compound in a survey scene comprising:
    collecting radiation from the survey scene with a lens element;
    passing the radiation collected from the survey scene through an optical band pass filter configured with a transmittance profile having a peak transmittance and a full width half maximum transmittance spectral bandwidth each falling within a wavelength range of 10.3 µm to 10.8 µm;
    focusing the radiation collected from the survey scene and filtered by the optical band pass filter onto a focal plane comprising an active area formed by a two dimensional array of quantum well infrared photo detectors (QWIPs) each having an active surface and each generating a photo current responsivity profile in response to an irradiance at the active surface, wherein the QWIPs are tuned using alternating layers of quantum wells and barriers to have a photo current responsivity profile having a peak response within a wavelength range of 10.4 µm to 10.8 µm and a full width half maximum spectral bandwidth of less than 0.7 µm;
    reading out analog photo current values from each QWIP; and
    converting the analog photo current values to corresponding digital signal values; and
    rendering a video image corresponding to the digital signal values, wherein the less than 0.7 µm spectral bandwidth of the focal plane array is selected to reduce signal noise substantially outside the wavelength range of 10.4 µm to 10.8 µm associated with the optical band pass filter and/or the focal plane array.

10. The method of claim 9, further comprising cooling the focal plane array to an operating temperature of less than 65° K.

11. The method of claim 10 further comprising:
    formatting the video image for display on a display device; and,
    displaying the video image on a display device.

12. The method of claim 11 wherein the formatting the video image further comprises:
    generating video signals for displaying text or graphic information that may be informative to a user; and,
    displaying the video signals simultaneously with the video image.

13. The method of claim 12 further comprising repeating the following at a rate of 15 to 100 cycles per second:
    reading out analog photo current values from each QWIP;
    converting the analog photo current values to corresponding digital signal values;
    rendering a video image corresponding to the digital signal values;
    formatting the video image for display on the display device; and,
    displaying the video image on the display device.

14. The method of claim 13 further comprising:
    pointing the camera system at a survey scene that may include a gas leak plume comprising a compound having an absorption band that at least partially falls within the wavelength range of 10.4 µm to 10.8 µm; and,
    observing the display device to determine if there is a gas leak plume visible on the display device.

15. The method of claim 9, wherein:
    the passing the radiation collected from the survey scene through an optical band pass filter comprises passing the radiation collected from the survey scene through an optical band pass filter configured with a transmittance profile having a peak transmittance and a full width half maximum transmittance spectral bandwidth each falling within a wavelength range of 10.3 µm to 10.7 µm; and
    the less than 0.7 µm spectral bandwidth of the focal plane array is selected to reduce dark current associated with the optical band pass filter and/or the focal plane array.

16. The method of claim 15 further comprising:
    pointing the camera system at a survey scene that may include a gas leak plume comprising a compound having an absorption band that at least partially falls within the wavelength range of 10.3 µm to 10.7 µm; and,
    observing the display device to determine if there is a gas leak plume visible on the display device.

17. The method of claim 13 wherein the displaying the video image includes displaying a black and white grey scale image with different grey scale values corresponding with different analog photo current values.

18. The method of claim 13 wherein the displaying the video image includes displaying a color image with different colors corresponding with different analog photo current values.

* * * * *